(12) United States Patent
Artyushenko

(10) Patent No.: US 7,956,317 B2
(45) Date of Patent: Jun. 7, 2011

(54) FIBRE OPTIC PROBE

(76) Inventor: Viacheslav Artyushenko, Berlin (DE)

( * ) Notice: Subject to any disclaimer, the term of this patent is extended or adjusted under 35 U.S.C. 154(b) by 241 days.

(21) Appl. No.: 12/455,583

(22) Filed: Jun. 2, 2009

(65) Prior Publication Data

US 2010/0213357 A1  Aug. 26, 2010

(30) Foreign Application Priority Data

Feb. 26, 2009 (EP) .................................. 09153808

(51) Int. Cl.
*G02B 6/26* (2006.01)
(52) U.S. Cl. ............... 250/227.24; 385/43; 385/123; 385/127; 356/300; 356/301
(58) Field of Classification Search ............ 250/227.24; 385/43, 123, 127; 356/300, 301
See application file for complete search history.

(56) References Cited

U.S. PATENT DOCUMENTS

| | | | |
|---|---|---|---|
| 5,754,722 A | 5/1998 | Melling | |
| 6,144,791 A | 11/2000 | Wach et al. | |
| 6,246,817 B1 | 6/2001 | Griffin | |
| 2005/0084912 A1* | 4/2005 | Poponin | 435/7.1 |
| 2005/0265678 A1 | 12/2005 | Manyam et al. | |
| 2007/0024847 A1* | 2/2007 | Zambuto et al. | 356/300 |
| 2009/0073432 A1* | 3/2009 | Jalali et al. | 356/301 |
| 2009/0202191 A1* | 8/2009 | Ramachandran | 385/11 |
| 2009/0322557 A1* | 12/2009 | Robb et al. | 340/870.3 |

FOREIGN PATENT DOCUMENTS

| | | |
|---|---|---|
| DE | 10002106 | 8/2000 |
| DE | 10034220 | 1/2002 |

OTHER PUBLICATIONS

T.F. Cooney, et al; "Comparative Study of Some fiber-Optic Remote Raman Probe Designs. Part I: Model for Liquids and Transparent Solids"; The Society for Applied Spectroscopy, Baltimore, US, vol. 50, No. 7, Jul. 1, 1996, pp. 836-848.

* cited by examiner

*Primary Examiner* — Seung C Sohn
(74) *Attorney, Agent, or Firm* — Alfred A. Fressola; Ware, Fressola, Van Der Sluys & Adolphson LLP

(57) ABSTRACT

A bidirectional fiber optic probe comprises an optical in/out coupler and a single fiber or a bundle of fibers, each fiber having a proximal end and a distal end and a numerical aperture NA=sin θ. The numerical aperture NA describes the range of angles over which the optical fiber's proximal end can accept or emit light. The numerical aperture depends on the refractive index n of the fiber core and is given by NA=n sin* θ. θ is the acceptance angle being defined as the half angle of the acceptance cone of the fiber at its proximal end.

25 Claims, 4 Drawing Sheets

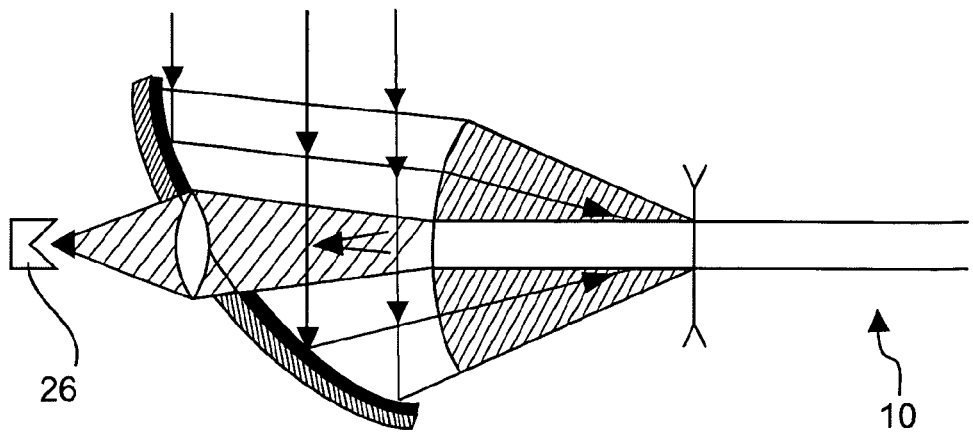
Fig. 6c
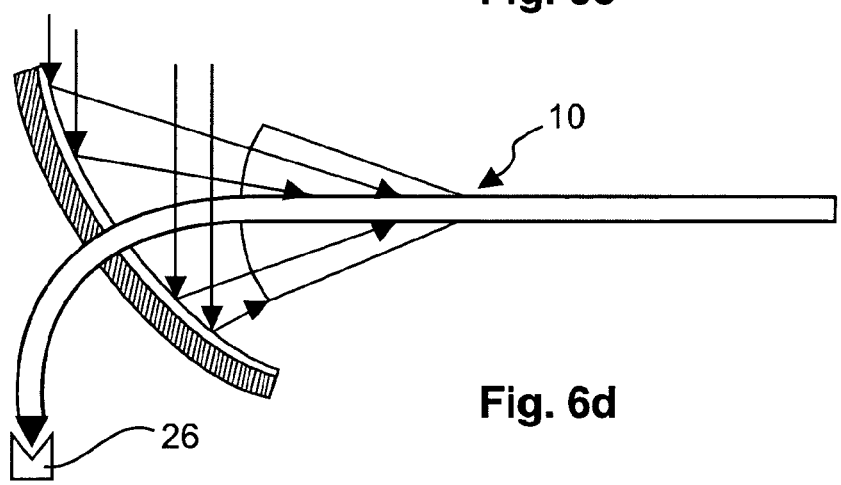
Fig. 6d
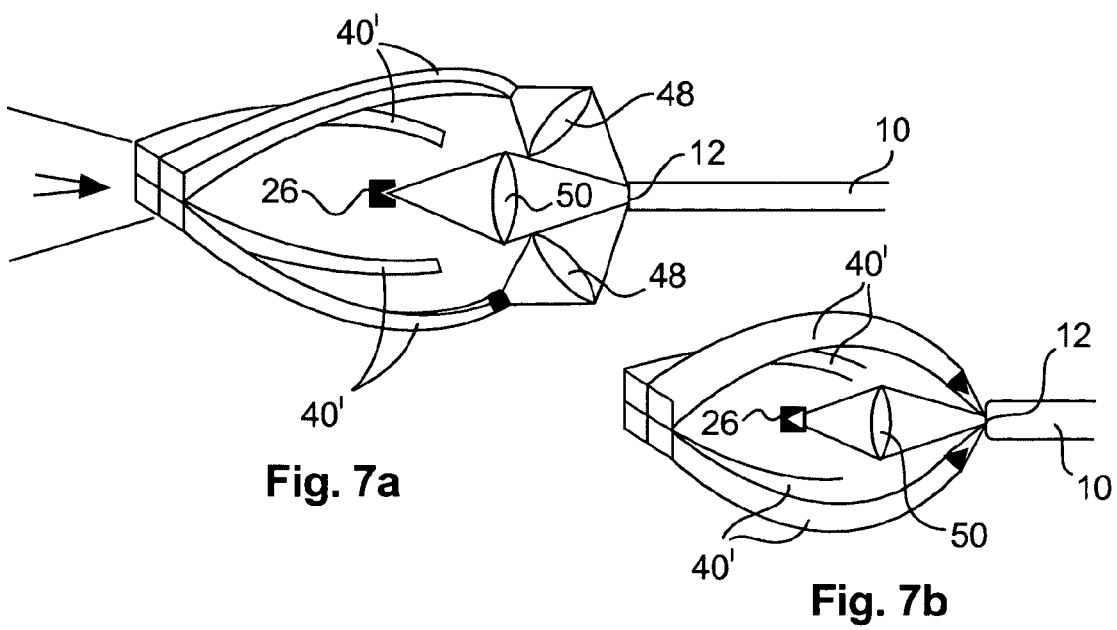
Fig. 7a
Fig. 7b

US 7,956,317 B2

FIBRE OPTIC PROBE

CROSS REFERENCE TO RELATED APPLICATION

This application claims priority under 35 USC §119 to European Patent Application No. EP 09153808.2 which was filed on Feb. 26, 2009.

TECHNICAL FIELD

The invention is directed to a fibre optic probe for use in spectroscopy. The probe comprises one or more fibres and an optical in/out coupler for coupling in and coupling out light into and from, respectively, the same optical fibre. The optical coupler is arranged at one end of the optical fibre or the bundle of fibres that hereinafter is called the proximal end.

BACKGROUND OF THE INVENTION

Fibre optic probes for spectroscopy are generally known in the art. In general such fibre optic probe comprises a first fibre or a first bundle of fibres to guide light from the proximal end of the probe to the distal end of the probe, and a second fiber or second bundle of fibers are used to guidelight back to the proximal end of the probe. An optical sensor element such as attenuated total reflectance sensor element or transmission/reflection (Trans-Reflex) element is arranged at the distal end of the fibre probe. The optical sensor element generally is arranged and adapted in a way that it interacts with a sample for determining the sample's spectroscopic properties so that light entering the optical sensor element is modified by the sample and is reflected back into the optical fibre of the bundle of optical fibres so it eventually is emitted out of the proximal end of the fibre or the bundle of fibres so they can be analyzed by an analyzing detector element such as spectrometer based on diffraction grating, Fourier Transform interferometer or spectral filter with a related photo element or array of detectors.

Examples for such probe are disclosed in U.S. Pat. No. 5,754,722.

SUMMARY OF THE INVENTION

It is an object of the invention to provide an improved spectroscopy probe that provides a high efficiency, small diameter and high flexibility.

According to the invention, this object is achieved by a bidirectional fibre-optic spectroscopic probe with an optical in/out coupler. The probe comprises a single fibre or a bundle of fibres, each fibre having a proximal end and a distal end and a numerical aperture NA=sin θ. The numerical aperture NA describes the range of angles over which the optical fibre's proximal end can accept or emit light. The numerical aperture depends on the refractive index n of the fibre core and is given by NA=n sin* θ. θ is the acceptance angle being defined as the half angle of the acceptance cone of the fibre at its proximal end.

The optical coupler is an in/out coupler arranged adjacent or near the proximal end for coupling light into said proximal end and for collecting light emerging from said proximal end of the fibre or the bundle of fibres. The bidirectional fibre optic spectroscopic probe further comprises an optical sensor element arranged adjacent or near said distal end of the fibre optic probe. The optical sensor element is adapted to sense a spectroscopic property of a sample to be brought into contact or in proximity to said sensor element.

The in/out coupler is arranged and adapted to couple higher mode light rays into the proximal end of the fibre and to let lower mode light rays pass to an analyzing sensor element. The optical in/out coupler comprises incoupling means that are adapted and arranged to couple light into said proximal end of said fibre or said bundle of fibres with an incidence angle between θ and θ/x, wherein x is in the range between 1 and 10. The optical in/out coupler further comprises outcoupling means that are adapted to collect light emerging from the proximal end of the fibre or bundled fibres with angles smaller than θ/x. Thus, the in/out optical coupler is adapted to couple higher-order modes of light into said fibre or bundle of fibres and to collect a relatively smaller-order mode of light emerging from said proximal end of said fibre or said bundle of fibres.

The fibre or each fibre of the bundle of fibres is adapted to operate as a converter that converts light modes of light propagating along the fibre from relatively higher-order modes to relatively lower-order modes. θ/x is the in/out separation angle. Each fibre can be seen as a spatial filter that attenuates said relatively higher order modes of light and redirect their power at least partly into said relatively lower order modes of light while the light propagates along said fibre and reflects from the distal end and said optical sensing element.

In other words, the claimed invention uses the effect that an optical fibre can concentrate and convert higher-order light modes into lower-order light modes while light travels along the fibres. This allows to couple in light with higher-order modes with relatively high energy and to regain a high-energy signal with lower light modes. Using the spatial filter characteristics allows for incoupling more light and thus a higher energy of light into said fibre while benefiting from the advantages of single fibre use to deliver light to the optical sensor element and thereafter reflected back to the probe's proximal end. All in all, the signal to noise ratio can be improved without the need to have two fibers, at least—as they are also used in common probes: one fiber to deliver light and the other to collect light back from the sensing element. Thus the need in two or more fibers in mixed fiber bundles is eliminated together with the need to use large size optical elements (like expensive Diamond ATR-elements). In result the probe diameter can be substantially reduced together with the price, while probe will be more flexible and can be used in mini-reactors, for human endoscopy and even inside blood vessels. Thus, the efficiency in the signal-to-noise ratio of the probe is improved while all the other probe parameters are substantially improved as well.

Further advantages result from the ability to use only a single fiber to deliver light to and collect light from the distal detector element for a single channel spectrometers. This invention is also applicable for multichannel spectrometers where each fiber is used as described above.

In a preferred embodiment, the fibre optical spectroscopic probe comprises a single fibre for guiding light coupled into said proximal end of said single fibre to said optical sensor element at its distal end of said single fibre and back from said optical sensor element to said proximal end of said single fibre. The single fibre is adapted to act as a propagating light mode converter from higher-order modes of light into lower-order modes of light, thus separating by means of the optical coupler the light coupled into said fibre from the light emerging from said fibre. The light coupled into said fibre is coming from a light source. The light emerging from said fibre has passed to the sensing element at the distal end of the fibre. Thus, the typical outcoupling efficiency of a fibre optic probe can be exceeded—in contrast to what can be achieved when using beam-splitters at the proximal fiber end or Y-fiber splitters, which provide a maximum efficiency that can not exceed 50% in the best case (see FIG. 5 to DE 10034220A1)

It is further preferred that the fibre optic spectroscopic probe comprises two or more fibres, wherein one fibre is used to record a reference spectrum and the other fibre is used for signal spectrum registration for spectral comparison, while each of two or more fibres is used in both guiding directions as described above. Such arrangement is preferred whenever a reference or background spectrum variation is possible and where a comparison of spectra between the signal spectrum and the background is required. Both of the at least two fibres operate bidirectional, while a dual channel spectrometer eliminates the need to measure, at first, background spectra and only then to measure signal spectra—which always requires calculation of these spectra ratio afterwords Dual (or multi) channel spectrometer with two or more bidirectional fiber probes enables the unique possibility of remote control for any process with background and signal spectra to be measured under the same conditions and in the same time preventing any drift and artifacts in control of important process parameters.

It is further preferred that the optical in/out coupler comprises a light guiding element or a light directing element that is adapted and arranged to let light emerging from said proximal end of said fibre in an angle between θ and θ/x, directly pass to an analyzing detector and to direct light emerging from a light source to be coupled into said fibre, so it enters the proximal end of the fibre in an angle between θ/x and θ.

A preferred embodiment of the in/out coupler comprises a light guiding element that is adapted and arranged to let light emitted by the proximal end of the fibre directly pass to an analysing detector element whereas light emitted from a light source is redirected so that it is directed to said proximal end of that fibre. In other words, the analysing detector element may be arranged inline with the fibre at its proximal end whereas the light source is arranged off the direct light path to the fibre proximal end and thus needs to be redirected in order to eventually hit the fibre proximal end. The light guiding element may comprise a mirror or even consist of mirror. Such arrangement allows feeding of all low order light modes emitted by the proximal fibre end to an analyzing detector element thereby avoiding unnecessary losses. Thus as much as possible of the light that is modified by the sample is used. On the other hand, incoupling efficiency can be lower since excess light can easily be provided by a common light source. In addition, means can be provided to collect more light from a large size light source and incouple the light into the fiber using a bundle of light incoupling fibers or fiber tapers designed for collection of light from a large size light spots as is pointed out in more detail with respect to FIGS. 6 and 7 below.

The light guiding element or elements or the light directing element or elements preferably comprise mirrors, lenses or fibres or a combination thereof.

In a particularly preferred embodiment, the optical in/out coupler comprises two or more mirrors. Alternatively, the light guiding in/out coupler comprises one or more lenses in combination with at least one mirror. In a further alternative embodiment, the light guiding optical in/out coupler comprises two or more mirrors in combination with one or more fibres.

Further preferred embodiments of the optical in/out coupler are disclosed in the following description of exemplary embodiments.

BRIEF DESCRIPTION OF THE DRAWINGS

The invention shall now be described based on exemplary embodiments depicted in the Figures. The Figures show in:

FIG. 6c/d: embodiments similar to FIG. 6b using a fiber having a conical cladding at its proximal end;
FIG. 7a: an optical in/out coupler using a combination of lenses and fibres;
and
FIG. 7b: another alternative embodiment of an optical in/out coupler using a combination of lenses and fibres.

DETAILED DESCRIPTION

Figure 1:
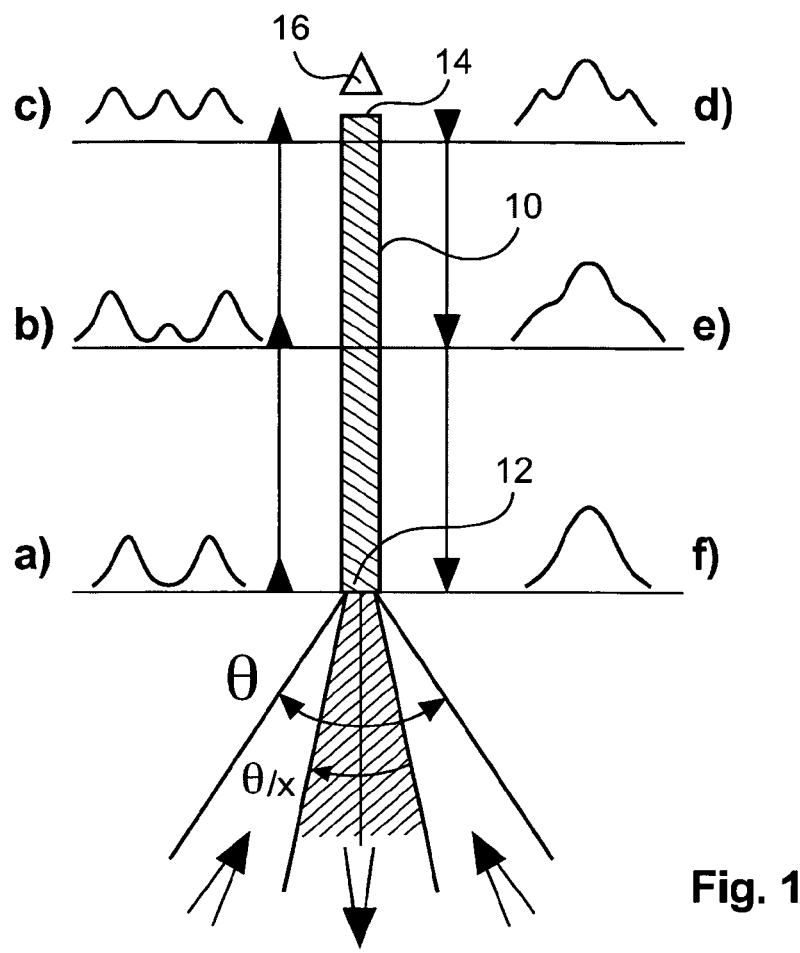
FIG. 1: An illustration of the inventive principle.

FIG. 1 illustrates the basic principle of the invention. A fibre 10 has an angle of acceptance θ. No light can be collected outside the cone defined by θ due to total reflection. According to the invention light shall be coupled into a proximal end 12 of fibre 10 with an angle greater than θ/2x. The light travels along the length of fibre 10 to its distal end 14. At the distal end 14, a spectroscopic sensor element 16 is arranged. The spectroscopic sensor element 16 can be a crystal that provides for an attenuated total reflection (ATR) of light entering the crystal and being reflected by the crystal back into the fibre 10 in a manner known as such. Attenuation of the reflected light in the crystal depends on the media adjacent to the crystal.

After having passed the spectroscopic sensor element 16, the light travels back along fibre 10 to its proximal end.

Fibre 10 comprises a core circumferentially surrounded with a cladding having a comparatively higher index of refraction. Typical core/cladding diameters could be, for example, 600 μm (core) and 700 μm (core incl. cladding) or 900/1000 μm, The numerical aperture (NA=n sin* θ, with θ: the acceptance angle and n: refractive index) could be between 0.22 or 0.3, but is not limited to these parameters.

Fibre 10 acts on the light travelling along fibre 10 as a spatial filter or mode-converter that converts higher order light modes into lower order light modes. Lower order light modes correspond to a smaller angle of propagation with respect to a central axis of fibre 10. Due to the mode-converting effect of fibre 10, a significant part of the light coupled into fibre 10 with a relatively high angle of inclination finally emerges from the proximal end 12 of fibre 10 with a relatively small angle of inclination.

Diagrams a) to f) of FIG. 1 illustrate the distribution of light propagation angles within fibre 10 and, more particular, a variation of a respective intensity profile for radiation propagating in optical fiber along its length—from its input to output ends with reflecting sensing element,—and for the radiation propagating back to the input end. The profiles in FIGS. 1a) to 1f) illustrate the profiles for the case that the input radiation profile a the proximal end of fiber 10 is a ring profile (but within fiber Numerical Aperture), while the output radiation is redistributed to the profile with the main power in smaller output angle.

FIG. 1a) is the distribution of light propagation angles of the light entering fibre 10 at its proximal end. FIG 1b) illustrates the distribution of light propagation angles of light travelling from the proximal end to the distal end 14 approximately halfway to distal end 14. FIG. 1c) is the distribution of light propagation angles of the light leaving fibre 10 at its distal end 14. FIG. 1d) is the distribution of light propagation angles of the light re-entering fibre 10 at its distal end 14 after having passed spectroscopic sensor element 16. FIG. 1e) illustrates the distribution of light propagation angles of light travelling back from distal end 14 to the proximal end 12 approximately half way to distal end 12. FIG. 1f) finally shows the distribution of light propagation angles of the light emerging from proximal end 12. The centre of each diagram corresponds to an angle of propagation with respect to the fibre central axis of zero.

From FIG. 1 it is apparent that a relatively high energy of light can be coupled into fibre 10 at a relatively high angle of inclination with respect to the fibre's central axis while still a significant portion of the light emerging from fibre 10 at the distal end 12 can be collected within relatively small angles of inclination. While the incoupling efficiency at higher angles of inclination corresponding to higher order light modes is not as good as the incoupling efficiency at lower angles of inclination corresponding to lower order light modes this no serious drawback since a surplus of light energy entering the fibre can easily provided without affecting the probe's efficiency and signal-to-noise ratio.

In order to achieve the effect illustrated in FIG. 1, an optical in/out coupler is provided at the proximal end 12 of fibre 10 (not shown in FIG. 1).

A variety of embodiments of such optical in/out coupler is illustrated in FIGS. 2 to 7.

Figure 2:
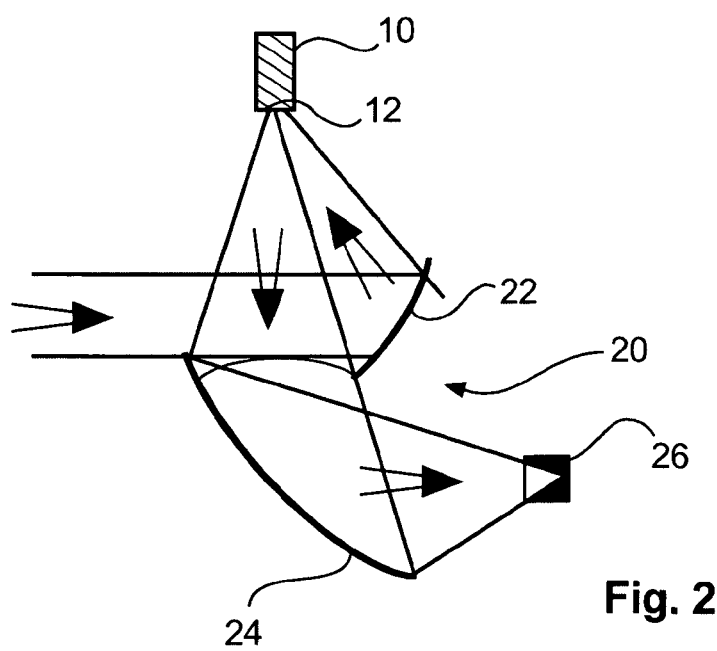
FIG. 2: a first exemplary embodiment of an optical in/out coupler according to the invention using mirrors.

In FIG. 2, an optical in/out coupler 20 composed of mirrors is illustrated schematically. The in/out coupler 20 is based on input beam (parallel) focusing with off-axis parabolic mirror 22 to the fiber proximal end under an angle to the fiber's longitudinal axis and to refocus an outcoming light beam on detector by means of an off-axis elliptical mirror 24. Thus, the first parabolic mirror 22 directs light emerging from a light source (not shown) to the proximal end 12 of fibre 10 so the light enters fibre 10 at an angle between θ and θ/x. The elliptic mirror 24 directs light emerging from the distal 12 with an angle between 0 and θ/x to a spectroscopic detector element 26.

The light source (not shown) can be an infrared heated black body (Globar) with or without a Fourier transformation interferometer. Alternatively, the light source can be a lamp, e.g. a tungsten lamp, a plasma lamp or another type of lamp. The light source could also be a laser to induce fluorescence or Raman scattering signal to be collected by in/out coupler from the proximal fibre end for its spectrum analysis. Further possible embodiments of the light source are a tunable laser or a light emitting diode (LED).

The spectroscopic detecting element can be an array of pyrodetectors (PDA), photodiodes, charged coupled devices (CCD) or the like. The spectroscopic detecting element can be provided with a diffraction grating. Further, the spectroscopic detecting element can be part of a Fourier transformation interferometer.

Figure 3:
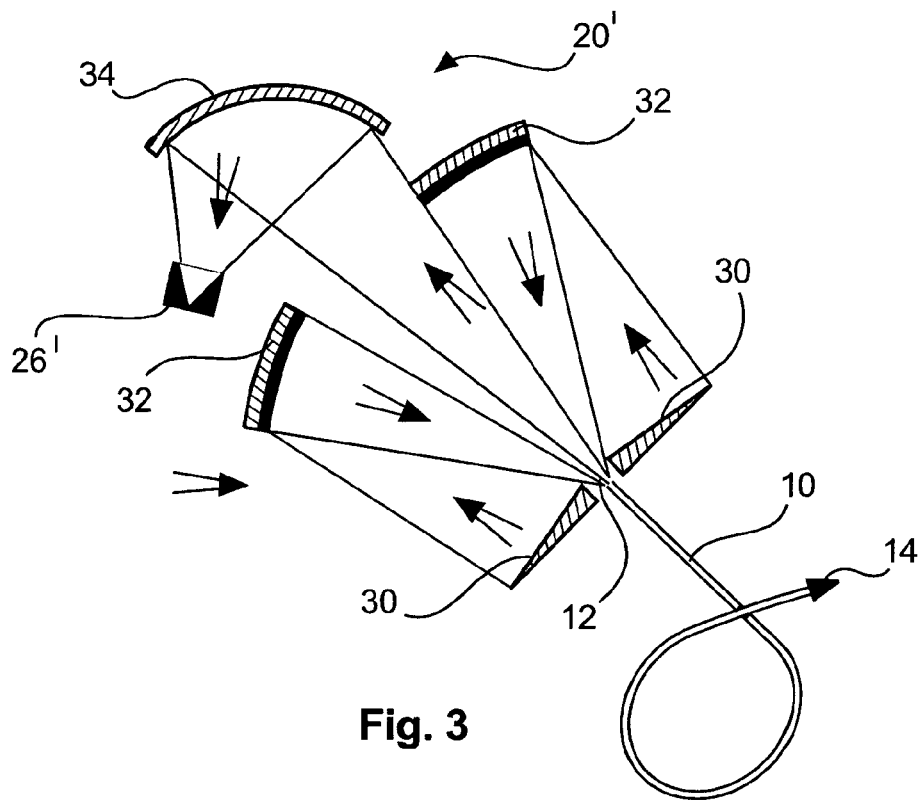
FIG. 3: an alternative embodiment of an optical in/out coupler using mirrors.

In FIG. 3, a different embodiment of an optical in/out coupler 20' composed of mirrors is illustrated schematically featuring an axicon 30 for providing parallel incoming beam, a spherical ring mirror 32 for focusing this beam onto the proximal fiber end and an off-axis elliptical mirror 34 for refocusing the outcoming beam onto a detector with. Thus, the optical in/out coupler 20' according to FIG. 3 comprises the axicon mirror 30 arranged around the proximal end 12 of fibre 10 and adapted to reflect light from a light source (not shown) to the first spherical ring mirror 32 that further reflects the light from the light source to the proximal end of fibre 10. The spherical ring mirror 32 has a central opening so light emerging from the proximal end 12 of fibre 10 can pass to the off-axis elliptical mirror 34 that directs the light emerging from proximal end 12 of fibre 10 to a spectroscopic sensor element 26'. The central opening in the spherical ring mirror 32 has a diameter that corresponds to the width of the cone defined by the angle θ/x. The total diameter (outer diameter) of the spherical ring mirror 32 corresponds to the cone defined by θ.

Figure 4:
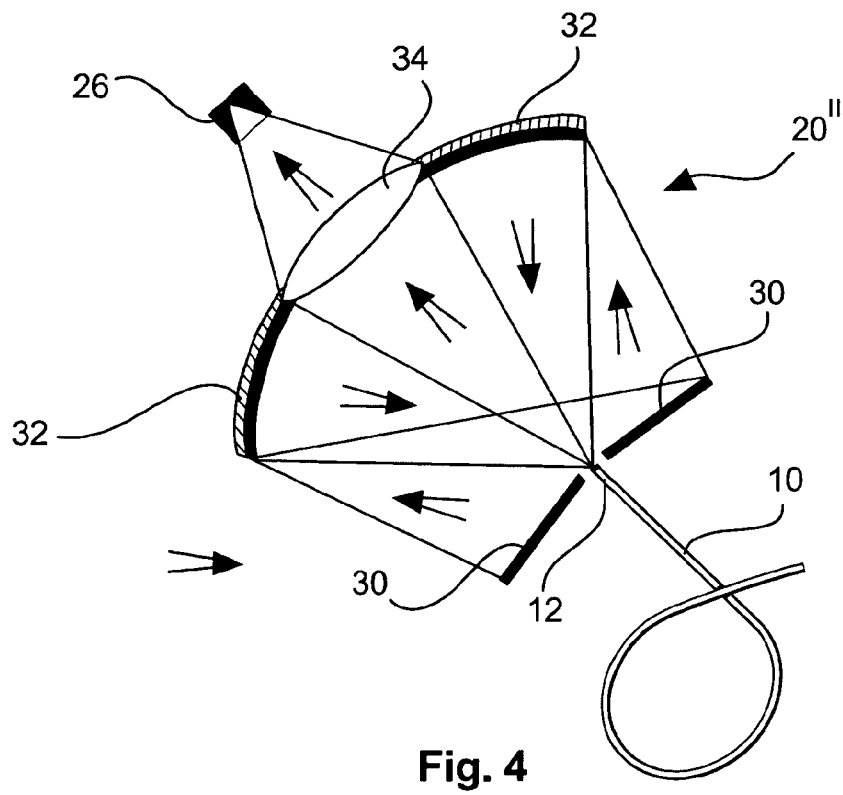
FIG. 4: an embodiment of an optical in/out coupler using a combination of mirrors and lenses.

FIG. 4 shows an optical in/out coupler 20" similar to the design shown in FIG. 3 with respect to the incoupling light path same as FIG. 3, but using a refocusing lens instead of off-axis elliptical mirror. The incoupling light path comprises an axicon mirror 30 arranged around to the proximal end 12 of fibre 10 reflecting light to be coupled into the fibre to a spherical ring mirror 32 that redirects the light to the proximal end 12 of fibre 10. Light emerging from the proximal end 12 of fibre 10 is, however, collected by a lens 36 that preferably is arranged in the central opening of the spherical ring mirror 32. The lens 36 focuses the light emerging from proximal end 12 of fibre 10 to the spectroscopic detector element 26.

Figure 5:
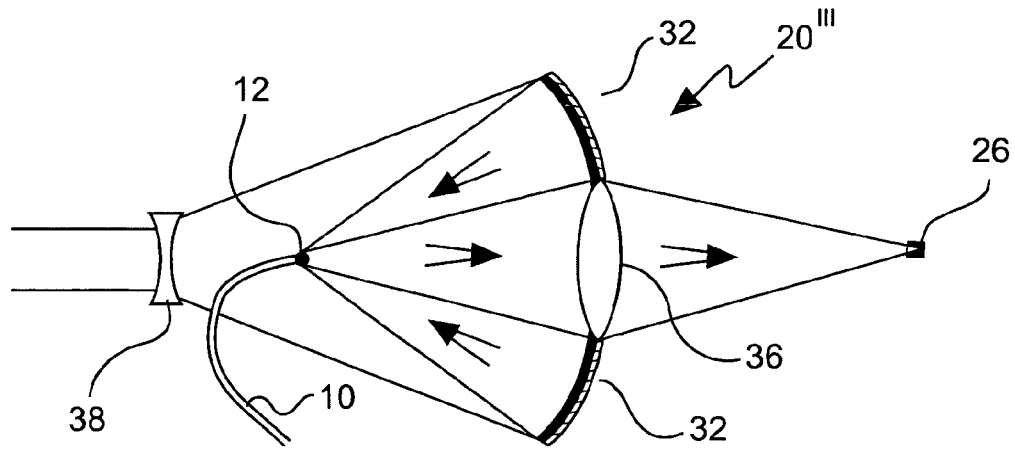
FIG. 5: an optical in/out coupler using a combination of lenses and mirrors in an alternative arrangement.

FIG. 5 illustrates an optical in/out coupler 20''' that is similar to the optical in/out coupler 20" illustrated in FIG. 4 with respect to the outcoupling light path in that the outcoupling light path comprises a collecting lens 36 that focuses the light emerging from the proximal end 12 of fibre 10 onto the spectroscopic detector element 26. In the incoupling light path, the axicon mirror is replaced by a diverging lens 38. The diverging lens 38 directs the collimated light emitted by a light source to the spherical ring mirror 32 surrounding the collecting lens 36.

Instead of the diverging lens 38, an axicon could be provided.

Figure 6A:
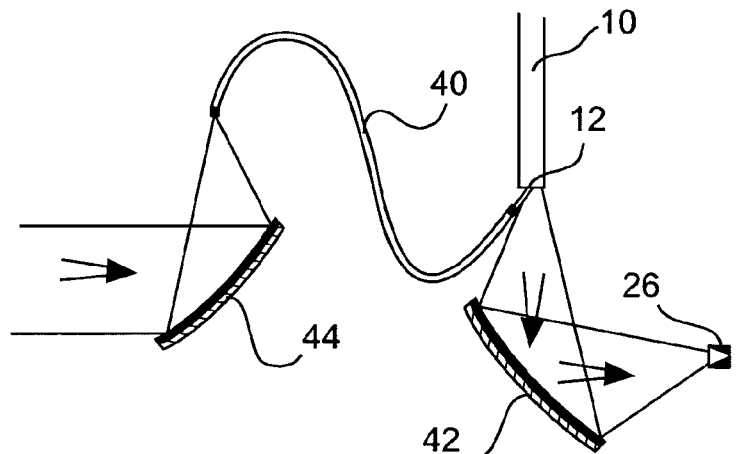
FIG. 6a: an optical in/out coupler using a combination of mirrors and fibers.

In FIGS. 6a) to 6d) it is illustrated, how an auxiliary fibre 40 can be used to either feed light into proximal end 12 of fibre 10 (FIG. 6a) or to direct light emerging from proximal end 12 of fibre 10 to the spectroscopic sensor element 26. Elliptical mirrors 42, 44 and 46 assist in redirecting and collecting the light.

Figure 6B:
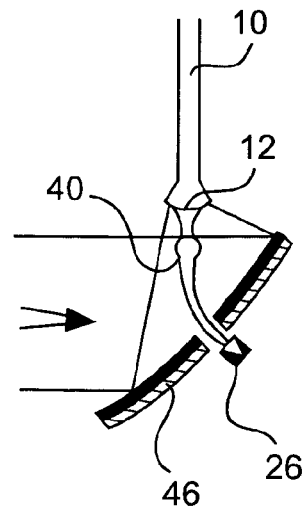
FIG. 6b: an alternative embodiment of an optical in/out coupler using a fibre and a mirror.

According to FIG. 6a) two off-axis mirrors are provided and an additional fiber with flat fiber end or with a distal end shaped as microlens;

The embodiment according to FIG. 6b) is similar to the embodiment of FIG. 6a), but with a single off-axis mirror and hole for output fiber;

The embodiment according to FIG. 6c) is similar to the embodiment of FIG. 6b), but using a conical taper made from fiber cladding material to increase light power coupling into the fiber core, while output radiation is refocused by the lens fixed in the central hole of off-axis mirror;

The embodiment according to FIG. 6d) is similar to the embodiment of FIGS. 6b) and 6c), but with a single fiber and conical taper used to collect and launch max power into fiber probe from IR-source and/or a fourier-transformation-interferometer after the source or before the detector.

FIGS. 7a and 7b illustrate further alternative embodiments wherein the light to be fed into the proximal end 12 of fibre 10 is guided by a plurality of auxiliary fibres 40' and is fed into proximal end 12 of fibre 10 from a plurality of directions. The auxiliary fibres 40' could be four square PIR-fibers with 1×1 mm cross-section.

According to FIG. 7a collecting lenses 48 are provided to focus the light to be fed into proximal end 12 of fibre 10 on said proximal end 12. According to FIG. 7b, each distal end of the auxiliary fibres 40' is shaped as microlens thus eliminating the need to use 4 refocusing lenses as in the embodiment according FIG. 7a).

In FIGS. 7a and 7b a collecting lens 50 is arranged in the out coupling light path focussing the light emerging from proximal end 12 of fibre 10 into the spectroscopic detector element 26 similar to the embodiments in FIG. 4 and FIG. 5.

FIGS. 2 to 7 are examples for optical in/out couplers composed of mirrors, lenses and/or fibres. The man skilled in the out can easily derive further arrangements for achieving a similar effect.

What is claimed is:

1. A bidirectional fibre optic spectroscopy probe comprising:
    a single fibre or bundle of fibres, each fibre having a proximal and a distal end and having a numerical aperture $NA = n*\sin\theta$, with $\theta$ being the acceptance angle that is the half angle of the acceptance cone of the fibre at its proximal end,
    an optical in/out coupler arranged adjacent or near said proximal end for coupling light into said proximal end of said fibre or bundle of fibres and for collecting light emerging from said proximal end, and
    an optical sensor element arranged adjacent or near said distal end and being adapted to sense a spectroscopic property of a sample to be brought in contact or in proximity to said sensor element
    characterized in that
    said in/out coupler has
    incoupling means that are adapted and arranged to couple light into said proximal end of said fibre or bundle of fibres with an incidence angle between $\theta$ and $\theta/x$, wherein x is in the range from >1 to 10, and
    outcoupling means that are adapted to collect light emerging from said proximal end of said fibre with an angle smaller than $\theta/x$,
    to thus enable the optical in/out coupler to couple higher order modes of light into said fibre or bundle of fibres and to collect back relatively lower order modes of light emerging from said proximal end of said fibre or bundle of fibres,
    wherein said fibre is adapted to operate as a converter of a propagating light modes from said relatively higher order modes of light into said relatively lower order modes of light.

2. The fibre spectroscopy probe according to claim 1, comprising a single fibre for guiding light coupled into said proximal end of said single fibre to said optical sensor element at said distal end of said single fibre and back from said optical sensor element at said distal end of said single fibre to said proximal end of said single fibre, said single fibre being adapted to act as a propagating light modes converter from higher modes of light into lower order modes of light thus separating together with the optical in/out coupler the light coupled into said fibre from a light source from the emerging light that returned back from the sensing element through the same fibre and that is directed by said optical in/out coupler to a detector.

3. The fibre spectroscopy probe according to claim 2 comprising of two or more fibres where one fibre is arranged to be used for reference spectrum recording and the other fibre is arranged to be used for signal spectrum registration to thus allow spectra comparison, wherein each fibre operates bi-directionally.

4. The fibre spectroscopy probe according to claim 1, wherein said optical in/out coupler comprises a light guiding element that is adapted and arranged to let light emerging from said proximal end of said fibre in the angle range from 0 to $\theta/x$ pass to an analyzing detector element and to direct light emerging from a light source to said proximal end of said fibre in the angle range from $\theta/x$ to $\theta$.

5. The fibre spectroscopy probe according to claim 4, wherein said light guiding optical in/out coupler comprises of two or more mirrors.

6. The fibre spectroscopy probe according to claim 4, wherein said light guiding optical in/out coupler comprises of one or more mirrors and one or more lenses.

7. The fibre spectroscopy probe according to claim 4, wherein said light guiding optical in/out coupler comprises of two or more mirrors and one or more fibres.

8. The fibre spectroscopy probe according to claim 4, wherein said light guiding optical in/out coupler comprises one or several fibers assembled in bundle to collect more light from the source and deliver it to the proximal fiber probe end and has refocusing lenses, mirrors or fiber ends shaped as microlenses for this purpose.

9. The fibre spectroscopy probe according to claim 4, wherein said light guiding optical in/out coupler comprises one or more conical tapers or prisms shaped for the most effective collection of light from the source, made from the material of fiber probe cladding and optically attached to said fiber probe cladding, and comprises either refocusing lenses or mirrors or fiber itself which may be terminated directly to the detector to focus returning from the distal sensing element and coming out of the proximal probe end onto said detector element and using.

10. The fibre spectroscopy probe according to claim 1, wherein said optical sensor element at distal fibre end is an attenuated total reflectance (ATR) sensor element.

11. The fibre spectroscopy probe according to claim 1, wherein said optical sensor element is a dual pass transmittance cell for liquids comprising reflecting mirror element.

12. The fibre spectroscopy probe according to claim 11, wherein said optical sensor element is a transmittance dual pass cell for gases with a collimating lens and reflecting mirror (Trans-Reflex) sensor element.

13. The fibre spectroscopy probe according to claim 10, wherein said optical sensor element is a multi-pass transmittance cell for gases with the collimating lens and set of reflecting mirrors (Trans-Reflex) sensor element.

14. The fibre spectroscopy probe according to claim 4, wherein said light source is an infrared heated black body (Globar).

15. The fibre spectroscopy probe according to claim 14, wherein said light source is part of or comprises a Fourier transformation interferometer.

16. The fibre spectroscopy probe according to claim 4, wherein said light source is a lamp.

17. The fibre spectroscopy probe according to claim 4, wherein said light source is a laser that is adapted to induce fluorescence or Raman scattering signal that can be collected by the optical in/out coupler from the proximal fibre end for spectrum analysis.

18. The fibre spectroscopy probe according to claim 4, wherein said light source comprises a tunable laser.

19. The fibre spectroscopy probe according to claim 4, wherein said light source comprises at least a light emitting diode.

20. The fibre spectroscopy probe according to claim 4, wherein said spectroscopic detecting element comprises a single or a dual pyrodetector, a photodiode or the like.

21. The fibre spectroscopy probe according to claim 4, wherein said spectroscopic detecting element comprises an array of pyrodetectors, photodiodes, charge coupled devices or the like.

22. The fibre spectroscopy probe according to claim 21, wherein said spectroscopic detecting element comprises a diffraction grating.

23. The fibre spectroscopy probe according to claim 4, wherein said spectroscopic detecting element is part of a Fourier transformation interferometer.

24. The fibre spectroscopy probe according to claim 20, wherein said spectroscopic detecting element comprises a diffraction grating.

25. The fibre spectroscopy probe according to claim 1 comprising of two or more fibres where one fibre is arranged to be used for reference spectrum recording and the other fibre is arranged to be used for signal spectrum registration to thus allow spectra comparison, wherein each fibre operates bi-directionally.

* * * * *